Figure 1:
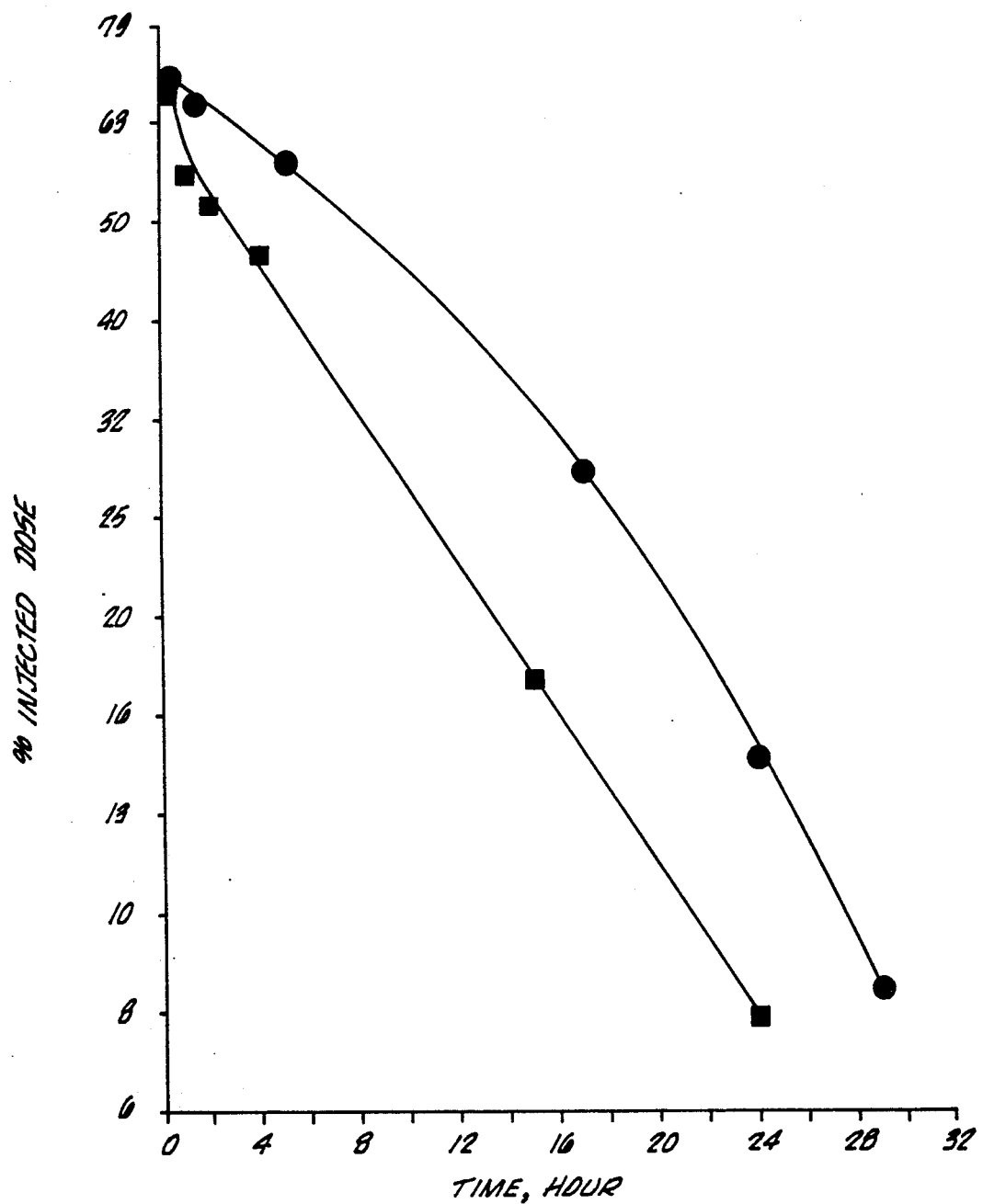

United States Patent [19]

Hwang

[11] Patent Number: 5,026,558
[45] Date of Patent: Jun. 25, 1991

[54] TARGETING DRUGS TO HEPATOCYTES IN THE LIVER

[75] Inventor: Karl J. Hwang, South Pasadena, Calif.

[73] Assignee: University of Southern California, Los Angeles, Calif.

[21] Appl. No.: 304,961

[22] Filed: Jan. 31, 1989

[51] Int. Cl.$^5$ ............................................. A61K 37/22
[52] U.S. Cl. .................................................... 424/400
[58] Field of Search .................. 424/450, 1.1; 264/4.3

[56] References Cited

U.S. PATENT DOCUMENTS

| | | | |
|---|---|---|---|
| 4,377,567 | 3/1983 | Geho | 424/1 |
| 4,569,926 | 2/1986 | Szabo et al. | 514/14 |
| 4,603,044 | 7/1986 | Geho et al. | 424/9 |
| 4,837,028 | 6/1989 | Allen | 424/450 |

FOREIGN PATENT DOCUMENTS

| | | |
|---|---|---|
| 180980 | 5/1986 | European Pat. Off. . |
| 62-201814 | 9/1987 | Japan . |

OTHER PUBLICATIONS

F. Roerdink, J. Dijkstra, G. Hartman, B. Bolscher, & G. Scherphof, "The Involvement of Parenchymal, Kupffer and Endothelial Liver Cells in the Hepatic Uptake of Intravenously Injected Liposomes. Effects of Lanthanum and Gadolinium Salts," *Biochim. Biophys. Acta* 677, 79-89 (1981).

H. H. Spanjer, H. Morselt, & G. L. Scherphof, "Lactosylceramide-Induced Stimulation of Liposome Uptake by Kupffer Cells in Vivo," *Biochim. Biophys. Acta* 774, 49-55 (1984).

H. H. Spanjer, M van Galen, F. H. Roerdink, J. Regts, & G. L. Scherphof, "Intrahepatic Distribution of Small Unilamellar Liposomes as a Function of Liposomal Lipid Composition," *Biochim. Biophys. Acta* 863, 224-230 (1986).

H. Essien, J. Y. Lai, & K. J. Hwang, "Synthesis of Diethylenetriaminepentaacetic Acid Conjugated Inulin and Utility for Cellular Uptake of Liposomes," *J. Med. Chem.* 31, 898-901 (1988).

*Primary Examiner*—Merrell C. Cashion, Jr.
*Assistant Examiner*—P. L. Prater
*Attorney, Agent, or Firm*—Michael B. Farber

[57] ABSTRACT

An improved method for selectively targeting a substance either to the parenchymal cells or the non-parenchymal cells of the liver makes use of the property that there are two pathways for uptake of liposomes by the liver: a saturable pathway involving phagocytosis and mediated by the Kupffer cells, and a non-saturable pathway involving pinocytosis and mediated by the parenchymal cells. The substance to be targeted is administered in carrier liposomes having a diameter of less than about 200 nm and a half-life in the circulation of at least about 5 hours as measured at an injection dose of about 30-50 micrograms of lipid per gram of body weight. The substance can be targeted to the parenchymal cells by administering it in carrier liposomes at a liposomal lipid dose expressed in micrograms of lipid per gram of body weight at least equal to a critical liposomal lipid dose, typically about 7 micrograms per gram of body weight to about 10 micrograms per gram of body weight. The substance can also be targeted to the parenchymal cells by selectively blocking the saturable pathway by the action of a blocking agent. The substance can be targeted to the non-parenchymal cells by administering it in carrier liposomes at a dose sufficiently lower than the critical lipid dose, typically 0.30 μg of lipid per gram of body weight or less. The substance can be a polypeptide, a polynucleotide, a carbohydrate, or a drug, such as an antiviral drug.

23 Claims, 1 Drawing Sheet

TARGETING DRUGS TO HEPATOCYTES IN THE LIVER

BACKGROUND

This invention was made with government support under 5 RO1 DK34013 awarded by the National Institute of Diabetes and Digestive and Kidney Diseases. The government has certain rights in the invention.

The invention is directed to methods of targeting substances, including drugs, to specific types of liver cells, including hepatocytes.

An ability to specifically target pharmacological agents to hepatocytes, the major cell type in the liver, as well as to other cell types in the liver, would have important therapeutic implications in treating disorders and conditions affecting the liver. These disorders and conditions include viral infections such as hepatitis, viral-related conditions, and metabolic disorders, including disorders resulting from absent or defective genes or improper regulation of gene expression. Such a delivery mechanism could also be directed to the delivery of a specific factor that could regulate gene expression in hepatocytes. Such factors could possibly convert hepatocytes to perform some function that they do not normally carry out, such as secreting insulin.

The cells of the liver can be divided into two general classes: (1) hepatocytes or parenchymal cells; and (2) non-hepatocytes or non-parenchymal cells. The hepatocytes perform most of the metabolic functions of the liver. The non-hepatocytes include several cell types, including Kupffer cells. The Kupffer cells carry out phagocytosis.

Previous attempts to achieve such specific targeting have focused on using agents containing terminal galactose as a homing device for delivering drugs and other substances of interest to hepatocytes. There have been two basic approaches for using terminal galactose.

The first approach is direct conjugation of a functional group containing terminal galactose to the substance of interest. This procedure suffers from the need to develop a specific conjugation procedure for each substance of interest. Also, it can be difficult to perform the conjugation without impairing the pharmacological or physiological activity of the substance. Many conjugation reactions employ organic solvents, severe conditions such as high temperatures, or reagents such as glutaraldehyde that can inactivate labile substances such as polypeptides. Conjugation can also affect the immunogenicity of the substance, bringing about undesired allergic reactions or eliciting antibodies against it that can neutralize it.

The second approach has been the encapsulation of the substance of interest in a particulate carrier containing terminal galactose, such as liposomes or low density lipoproteins. This technology is used in U.S. Pat. No. 4,377,567 to Geho, U.S. Pat. No. 4,603,044 to Geho et al., Japanese Patent Publication No. 62201814, assigned to Daiichi Seiyaku, K. K. and Japanese Patent Publication No. 61112021 by Tomikawa et al.

This second approach has been disappointing. According to recent reports, a galactose receptor similar to that present on the surface of hepatocytes also exists on the surface of Kupffer cells. The ultimate cellular destination of carriers containing terminal galactose therefore depends on the number and positioning of the galactose groups on the surface of the carriers. The destination of the carrier is not readily predictable from the carrier used, the group conjugated, or the method of conjugation. Also, as with the method of direct conjugation to the substance, the conjugation of galactosyl groups to the surface of particulate carriers can result in adverse immunological reactions.

Other work has shown that there is a distribution of administered liposomes between parenchymal and non-parenchymal cells and that at high total dosages of liposomal lipid, at least 15-20 micrograms of liposomal lipid per gram of body weight, the liposomes are taken up predominantly by the parenchymal cells. This work includes F. Roerdink, J. Dijkstra, G. Hartman, B. Bolscher, & G. Scherphof, "The Involvement of Parenchymal, Kupffer and Endothelial Liver Cells in the Hepatic Uptake of Intravenously Injected Liposomes. Effects of Lanthanum and Gadolinium Salts," *Biochim. Biophys. Acta* 677, 79-89 (1981); H. H. Spanjer, H. Morselt, & G. L. Scherphof, "Lactosylceramide-Induced Stimulation of Liposome Uptake by Kupffer Cells in Vivo," *Biochim. Biophys. Acta*, 774, 49-55 (1984); and H. H. Spanjer, M. van Galen, F. H. Roerdink, J. Regts, & G. L. Scherphof, "Intrahepatic Distribution of Small Unilamellar Liposomes as a Function of Liposomal Lipid Composition," *Biochim. Biophys. Acta* 863, 224-230 (1986). However, the use of such excessively high doses of liposomal lipids results in a waste of liposomal lipid and substance to be carried, and may be undesirable for other reasons, such as not being suitable for those patients harmed by high dosages of lipids. This group includes patients with hyperlipidemias and certain other disorders.

Accordingly, there is a need for an improved method for selectively targeting substances such as drugs to classes of liver cells, especially hepatocytes. The method should avoid conjugation of galactose residues to either the substance to be carried or the carrier, prevent the occurrence of undesirable immunological reactions, be readily predictable in its effects, and avoid the administration of excess lipid.

SUMMARY

Improved methods for selectively targeting a substance to either the parenchymal or the non-parenchymal cells of the liver, according to the present invention, meet these needs. These methods use carrier liposomes with certain defined characteristics to carry the substance to be selectively targeted.

When it is desired to selectively target the substance to the parenchymal cells of the liver of a human or animal body, the method, in general, comprises the steps of:

(1) administering to the body a blocking agent for at least partially blocking uptake of liposomes by non-parenchymal cells of the liver; and (2) administering into the body the substance in carrier liposomes, the carrier liposomes being stable at 37° C. in serum, having a diameter of less than about 200 nm, and having a half-life in the circulation of the body of at least about 5 hours as measured at an injection dose of about 30-50 micrograms of lipid per gram of body weight, the substance being taken up predominantly by the parenchymal cells.

Each liposome has a critical liposomal lipid dose, defined as the liposomal lipid dose at which at least 75% of the liposomes administered to the body are taken up by the hepatocytes. Typically, the critical liposomal lipid dose is between about 7 micrograms per gram of body weight and about 10 micrograms per gram of body weight.

The step of administering the blocking agent can comprise administration of an agent specifically inhibiting phagocytic activity. The blocking agent can be liposomes with a diameter of greater than about 200 nm, carbon particles, or heat-damaged or aged erythrocytes.

Preferably, the carrier liposomes are unilamellar and neutral, and are composed of a mixture of sphingomyelin and cholesterol or a mixture of a phosphatidylcholine and cholesterol. More preferably, the phosphatidylcholine in the liposomes is distearoylphosphatidylcholine.

The substance to be selectively targeted can be a polynucleotide, a polypeptide, a carbohydrate, or a drug, such as an antiviral drug.

As an alternative to the use of a blocking agent, the method can comprise administering into the body the substance in carrier liposomes, the carrier liposomes having a diameter of less than about 200 nm and having a half-life in the circulation of at least about 5 hours as measured at an injection dose of about 30-50 micrograms of lipid per gram of body weight. The carrier liposomes are administered in a total quantity of lipid per unit of body weight at least equal to the critical liposomal lipid dose but less than about 15 micrograms of lipid per gram of body weight. The substance is taken up predominantly by the parenchymal cells.

When it is desired to selectively target the substance to non-parenchymal cells, the method can then comprise administering to the body the substance in carrier liposomes. The carrier liposomes have a total quantity of lipid per unit of body weight sufficiently lower than the critical liposomal lipid dose. The substance is then taken up predominantly by the non-parenchymal cells.

DRAWING

These and other features, aspects, and advantages of the present invention will become better understood with reference to the following description, appended claims, and accompanying drawing where:

The single figure is a profile of the clearance of SM-CH SUV at high and low dose ranges.

DESCRIPTION

A. Two Pathways of Liposomal Uptake

In developing an improved procedure for the selective targeting of a substance to either the hepatocytes or the non-hepatocytes of the liver of a mammalian body, it has been discovered that the hepatic uptake of certain types of liposomes can occur by dual, parallel pathways. The first pathway, designated "pathway A" herein, is a saturable, phagocytic pathway of uptake mediated by Kupffer cells, one of the significant types of non-hepatocytes or non-parenchymal cells. The second pathway, designated "pathway B" herein, is a non-saturable, pinocytotic pathway of uptake mediated by the hepatocytes, also known as the parenchymal cells.

The liposomes under this dual-pathway control of uptake have several characteristics. Liposomes with these characteristics are generally referred to herein as "carrier liposomes." They are stable in serum at 37° C. They are small, preferably less than about 200 nm in diameter. They resist rapid phagocytic uptake by cells of the reticuloendothelial system such as phagocytic macrophages and blood monocytes, thereby surviving in the circulation with a half-life of at least about 5-10 hours, as measured at an injection dose of about 30-50 micrograms of lipid per gram of body weight. Preferably, such liposomes are unilamellar and neutral in composition, although liposomes composed of positively-charged or negatively-charged liposomes can also be used. Typically the liposomes used are composed of an about 2:1 mixture of sphingomyelin and cholesterol, the ratio being the molar ratio of the two lipid components, or of an about 2:1 mixture of a phosphatidylcholine and cholesterol. Mixtures of these compositions or derivatives of them can also be used. Typically the sphingomyelin in such liposomes is bovine brain sphingomyelin, and the phosphatidylcholine is distearoylphosphatidylcholine.

The substance to be selectively targeted is incorporated into carrier liposomes with the desired characteristics and under dual-pathway control of uptake. Preferably, the substance is hydrophilic so that it does not leak through the lipid bilayer of the liposome, although lipophilic substances can be targeted at lower efficiency. For example, and not by way of limitation, the substance can be a polypeptide, such as a protein or a peptide hormone, or the peptide antiviral agent interferon. The protein can be an enzyme lacking or deficient in the liver, such as hypoxanthine-guanine phosphoribosyltransferase in the inherited neurologic disorder Lesch-Nyhan syndrome. The substance can also be a polynucleotide, such as a segment of DNA carrying the gene for a particular function and produced by techniques well-known in the art, such as recombinant DNA technology or polynucleotide synthesis. The substance can also be a carbohydrate or a drug, such as an antiviral agent for the treatment of such viral diseases as hepatitis.

In accordance with this discovery, the carrier liposomes can be selectively targeted to hepatocytes by one of several different procedures, as detailed below.

The first of these procedures involves the determination of a dosage level of liposomal lipid per unit of body weight designated as the critical liposomal lipid dose. When carrier liposomes that are under dual-pathway control are administered to a mammalian body at a dosage level at least equal to the critical liposomal lipid dose, but less than about 15-20 micrograms of lipid per gram of body weight, the saturable pathway is at least partially blocked and the carrier liposomes are then taken up predominantly by the parenchymal cells, delivering the substance.

Conversely, when the dosage level is sufficiently below the critical liposomal lipid dose, pathway B is not fully activated and the carrier liposomes are taken up predominantly to the non-hepatocytes when administered to a human or animal body, again delivering the substance to be targeted.

The second of these procedures involves the administration to the body of a blocking agent that can at least partially block pathway A regardless of the dosage level of the carrier liposomes. This procedure can be used even when the dosage level of the carrier liposomes is below the critical liposomal lipid dose.

B. Targeting by Dosage Level

1. Targeting of Hepatocytes

As mentioned above, one convenient way of targeting the substance to the hepatocytes of a mammalian body, including a human body, is the administration of the carrier liposomes in a dosage greater than the critical liposomal lipid dose. The administration can be by means of any method allowing the administered liposomes access to the bloodstream, such as intravenous or intraperitoneal injection. This technique is possible because the distribution of such liposomes between hepatocytes and non-hepatocytes varies continuously and monotonically with the dosage level of the liposomes expressed in terms of the quantity of liposomal lipid in micrograms per gram of body weight. This distribution varies quite sharply with dosage level below about 10 μg lipid per gram of body weight. The critical liposomal lipid dose is defined as that liposomal lipid dose at which at least 75% of the liposomes administered to the body are taken up by the hepatocytes. For the types of liposomes used in the work reported herein, the critical liposomal lipid dose is typically between about 7 and about 10 μg lipid per gram of body weight.

As detailed below in the Examples, the critical liposomal lipid dose is determined experimentally by measuring the distribution of carrier liposomes between the parenchymal cells and the non-parenchymal cells. One method of performing this is by using liposomes carrying the inert carbohydrate inulin covalently coupled to $^{111}In^{3+}$-labeled diethylene triamine pentaacetic acid (DTPA). At 40 hours after administration, the liver is excised, the hepatocytes are separated from non-hepatocytes, including Kupffer cells and endothelial cells, and the radioactivity in each cell type is determined.

The substance to be delivered can then be selectively targeted to hepatocytes by administering it to a human or animal body in liposomes under dual-pathway control at a liposomal lipid dose per unit of body weight at least equal to the critical liposomal lipid dose. It is preferred, although not absolutely required, that the substance be administered in the same liposomes as those used to determine the critical liposomal lipid dose. However the critical liposomal lipid dose varies little for different types of liposomes under dual-pathway control.

In this procedure, the lipid dose is preferably less than about 125 micrograms of lipid per gram of body weight, more preferably less than about 50 micrograms per gram of body weight, and most preferably less than about 15 micrograms per gram of body weight.

One advantage of this method over previous methods is that once the critical liposomal lipid dose is reached, there is no need to increase the lipid dose further. This results in more economical use of scarce materials, including purified lipid and the substance to be targeted, and also prevents untoward effects caused by administration of excess lipid.

2. Targeting of Non-Hepatocytes

As shown in Example 2 below, it is also possible to selectively target a substance to be delivered to non-hepatocytes, including Kupffer cells and endothelial cells. This is accomplished by administering the substance in carrier liposomes at a dose sufficiently below the critical liposomal lipid dose that the liposomes are taken up predominantly by the non-hepatocytes. This dose is preferably less than about 0.3 μg of liposomal lipid per gram of body weight, more preferably less (than about 0.15 μg of liposomal lipid per gram of body weight, and most preferably less than about 0.1 μg of liposomal lipid per gram of body weight.

Targeting of non-hepatocytes can be useful if it is desired to administer drugs or other substances that could be toxic to hepatocytes. By targeting them to non-hepatocytes, it might be possible to administer such substances in higher and more effective doses than otherwise possible.

C. Targeting by Administration of Blocking Agent

Other techniques, not directly dependent on the dosage of the liposomes under dual-pathway control, can also be used to at least partially block pathway A. Any agent that can inhibit or overload the phagocytic activity of the reticuloendothelial system can be used to block the pathway, and selectively direct liposomes under dual-pathway control of uptake to the hepatocytes through pathway B. Such an agent is designated herein as a "blocking agent." In this alternative, the blocking agent is defined as not containing the substance to be targeted. Preferably the blocking agent can specifically inhibit phagocytic activity. Among these blocking agents are large liposomes, preferably multilamellar, of diameter greater than about 200 nm; carbon particles; and heat-damaged or aged erythrocytes. When such blocking agents are administered simultaneously with liposomes under dual-pathway control, the liposomes under dual-pathway control are selectively taken up by the hepatocytes, even at liposomal lipid dosages, such as 0.15 μg of lipid per gram of body weight, much less than the critical liposomal lipid dose. This is shown in Example 3.

EXAMPLES

Example 1

Preparation of Radiolabeled Inulin and Small Unilamellar Liposomes

In all Examples reported herein, inulin covalently conjugated with $^{111}In^{3+}$-labeled diethylene triamine pentaacetic acid (DTPA) entrapped in the aqueous compartment of small unilamellar liposomes (designated small unilamellar vesicles (SUV) herein for consistency with prior publications) was used as the marker of liposomes. The detailed procedure of the synthesis of DTPA-conjugated inulin is described in H. Essien, J. Y. Lai, and K. J. Hwang, "Synthesis of Diethylenetriaminepentaacetic Acid Conjugated Inulin and Utility for Cellular Uptake of Liposomes," *J. Med. Chem.* 31, 898–901 (1988), which is incorporated herein by this reference. Briefly, DTPA-inulin was prepared by a four-step synthetic sequence, starting from the preparation of DTPA-conjugated ethylenediamine and periodate-oxidized inulin. DTPA-conjugated ethylenediamine was prepared by reacting DTPA anhydride with a mono t-butoxycarbonyl derivative of ethylenediamine followed by deblocking the t-butoxycarbonyl group in trifluoroacetic acid and subsequent purification by column chromatography on the formate form of AG1-X8 cation exchange resin (BioRad). DTPA-conjugated inulin was obtained by reacting the periodate-oxidized inulin with DTPA-conjugated ethylenediamine followed by purification by chromatography on Whatman CM-52 carboxymethylcellulose cation exchange resin. The tight binding of DTPA-conjugated inulin with heavy metal cations, such as $^{111}In^{3+}$, was ascertained by quantitating the complex of DTPA-conjugated inulin with $^{111}In^{3+}$ eluted the void volume from a Sephadex ™ G-25 gel filtration column (0.8×110 cm) after incubating DTPA-conjugated inulin with $^{111}In^{3+}$-nitrilotriacetic acid at room temperature for 15 minutes prior to passage through the gel filtration column. The concentration of DTPA-conjugated inulin was estimated by the phenol-sulfuric assay described in J. E.

Hodge & B. T. Hofreiter, "Determination of Reducing Sugars and Carbohydrates," in *Carbohydrate Chemistry* (R. L. Whistler & M. L. Wolfram, eds., Academic Press, New York, 1962), vol. 1, pp. 380-394.

SUV were prepared by sonication of 20-25 mg of dried thin film of bovine brain sphingomyelin-cholesterol (2:1, mol/mol), or L-distearoylphosphatidylcholine-cholesterol (2:1, mol/mol) in 1 ml of 154 mM NaCl, 5 mM sodium phosphate, pH 7.4, containing 1 mM DTPA-conjugated inulin in a Branson ™ 350 sonicator for 15 minutes as described in K. Hwang, K.-F. S. Luk, & P. L. Beaumier, "Hepatic Uptake and Degradation of Unilamellar Sphingomyelin/Cholesterol Liposomes: A Kinetic Study," *Proc. Nat. Acad. Sci. U.S.A.* 77, 4030-4034 (1980). The sonication temperatures were 45° C. for sphingomyelin-cholesterol (SM-CH) and 65° C. for distearoylphosphatidylcholine-cholesterol (DSPC-CH). The titanium fragments and aggregates were removed from the sonicated liposomes by centrifugation at 10,000×g for 5 minutes. The average size of SM-CH liposomes was estimated to be 187±42 Å and that of DSPC-CH liposomes, 720±40 Å, from negative-stain electron micrographs of phosphotungstate-stained liposomes, as described in P. L. Beaumier, K. J. Hwang, & J. T. Slattery, "Effect of Liposome Dose on the Elimination of Small Unilamellar Sphingomyelin/Cholesterol Vesicles from the Circulation," *Res. Comm. Pathol. Pharmacol.* 39, 277-289 (1983). The SUV were annealed at their respective sonication temperatures for 30 minutes, and then separated from the unentrapped DTPA-conjugated inulin by passing them through a Sepharose ™ 6B CL gel filtration column (0.8×70 cm) that was equilibrated and eluted with 154 mM NaCl, 5 mM Tris-HCl, pH 7.6. The SUV were collected in the void volume. The phospholipid concentration was determined by ferrothiocyanate assay or by phosphate analysis.

Radiolabeling of liposome-entrapped DTPA-conjugated inulin with $^{111}In^{3+}$ was carried out essentially by the same method used for externally loading $^{111}In^{3+}$ by acetylacetone to liposome-entrapped nitrilotriacetic acid, as described in P. L. Beaumier & K. J. Hwang, "An Efficient Method for Loading Indium-111 into Liposome Using Acetylacetone," *J. Nucl. Med.* 24, 810-815 (1982). The $^{111}In^{3+}$-loaded liposomes were subsequently purified by passage over a column of AG1-X8 ion exchange resin (0.8×14 cm) that was equilibrated and eluted with 0.106 M sodium phosphate, pH 7.4 isotonic buffer as reported in H.-O. Choi & K. J. Hwang, "Application of Anion-Exchange Resin to Remove Lipophilic Chelates from Liposomes," *Anal. Biochem.* 156, 176-181 (1986). The percentage loading was estimated from the radioactivity associated with the purified liposomes and the total radioactivity applied to the column.

To ensure that the $^{111}In^{3+}$ was chelated by DTPA-conjugated inulin, an unloading procedure of inducing the release of the non-specifically bound $^{111}In^{3+}$ from liposomes by tropolone, an ionophore, was used. Liposomes entrapping $^{111}In^{3+}$-DTPA-conjugated inulin were incubated with 0.106 M sodium phosphate, pH 7.4, in the presence of 100 μM tropolone, 10 mM nitrilotriacetic acid (NTA) at room temperature for 20 minutes to induce the release of $^{111}In^{3+}$ ions that had not been chelated by DTPA-conjugated inulin. Liposomes were further purified by AG1-X8 ion-exchange chromatography as described above. Typically, 60-80% of the externally-added $^{111}In^{3+}$ can be encapsulated by SUV using the above ionophoric loading/unloading procedure.

Example 2

Distribution of SUV in Rat Livers

Female Sprague-Dawley rats, with mean body weight of about 200 grams, were used throughout. The purified SUV entrapping inulin-DTPA($^{111}In^{3+}$) were injected into a group of 3 to 5 rats via the tail vein. Each rat received a volume of about 200 μl of various concentrations of the SUV. The dose of SUV was expressed as μg of total liposomal lipid per gram of body weight. The injected rats were returned to their cages for a 40-hour resting period to allow the injected SUV to be cleared completely from their blood. At the end of the resting period, the rats were injected intraperitoneally with 50 mg Nembutal per kilogram of body weight and 50 units of heparin. A catheter was inserted into the hepatic portal vein of each anesthetized rat, and the inferior vena cava was cannulated via the right atrium. Immediately after the blood was drained from the mesenteric artery, the liver was perfused unidirectionally with Krebs-Henseleit buffer containing 1% bovine serum albumin, 0.2% glucose, 0.055% sodium pyruvate, 0.085% sodium gluconate, and 0.2% collagenase at 40 units/ml for 30 minutes at 37° C.

To study the cellular distribution of the liposomes in the liver, the parenchymal, Kupffer, and endothelial cells from the liver of each animal were fractionated. The parenchymal cells were isolated by a slight modification of the method of M. N. Berry & D. S. Friend, "High-Yield Preparation of Isolated Rat Liver Parenchymal Cells", *J. Cell. Biol.* 43, 506-520 (1969). The non-parenchymal cells were further fractionated into Kupffer and endothelial cells by the method of centrifugal elutriation, as described in D. L. Knook & E. C. H. Sleyster, "Separation of Kupffer and Endothelial Cells of the Rat Liver by Centrifugal Elutriation," *Exp. Cell Res.* 99, 444-449 (1976). Concomitantly, pure Kupffer cells were also isolated by treating the debris from the filtered, collagenase-perfused liver with protease according to a slight modification of the method of A. C. Munthe-Kass, T. Berg, P. O. Seglen, & R. Seljelid, "Mass Isolation of Culture of Rat Kupffer Cells," *J. Exp. Med.* 141, 1-10 (1975).

The collagenase-perfused liver was minced into small pieces and shaken for 10 minutes at 37° C. to loosen the cells prior to filtering the loosened cells through a double layer of nylon gauze. The filtered debris was used as the source for further isolation of pure Kupffer cells, while the loosened cell suspension was centrifuged at 50×g for 2 minutes at 4° C. The pellet from the low-speed centrifugation of the suspension, which contained mostly parenchymal cells, was washed twice by low speed centrifugation at 50×g for 2 minutes using Krebs-Henseleit buffer containing 1% bovine serum albumin, 0.2% glucose, and 2 mM $CaCl_2$.

The non-parenchymal cells were collected by centrifuging the supernatant of the cell suspension at 750×g for 10 minutes at 4° C. Further separation of endothelial and Kupffer cells was achieved by injecting the suspended non-parenchymal cells into a JE-6B centrifugal elutriator (Beckman Instruments, Inc., Fullerton, Calif.), centrifuging at 750×g and elutriating at a flow rate of 10 ml/min with Krebs-Henseleit buffer. Endothelial cells were then collected at an elutriating flow rate of 22 ml/min, and Kupffer cells at 55 ml/min. A volume of 500 ml of suspension was collected for each cell type.

Concomitantly, pure Kupffer cells were also isolated from the same liver by shaking the filtered debris of the collagenase-perfused liver with Krebs-Henseleit buffer containing 0.2 mg/ml protease (14 units/ml) at 37° C. for 30 minutes. Kupffer cells were collected by centrifuging the protease-digested mixture at 600×g for 10 minutes at 4° C. The pellet, which contained the loosened Kupffer cells, was washed twice by centrifugation at 600×g for 10 minutes at 4° C. using Krebs-Henseleit buffer containing 1% bovine serum albumin, 2% glucose, and 2 mM $CaCl_2$.

Cell numbers were counted on a hemocytometer. More than 95% of the cells excluded trypan blue, indicating their viability. Radioactivity associated with the cells was determined in a Packard gamma counter (Model 5002). Calculation of the total number of each cell type in a liver was based on the values of $450 \times 10^6$ parenchymal cells per 100 g of body weight, $48.5 \times 10^6$ Kupffer cells per 100 g of body weight, and $145.5 \times 10^6$ endothelial cells per 100 g of body weight. The percentages of Kupffer cell contamination in both parenchymal and endothelial cell suspensions were estimated by counting the cells showing positive peroxidase staining. In conjunction with the specific radioactivity in terms of CPM per cell of the pure Kupffer cells isolated by the method of protease digestion, the liposomal radioactivity associated with parenchymal and endothelial cells was obtained after correcting for the Kupffer-cell contamination. The data are shown in Table 1 for SM-CH SUV and in Table 2 for DPSC-CH SUV. For both types of SUV, at very low doses, the liposomes were predominantly taken up by non-parenchymal cells. By the time the dose reaches about 7 μg of liposomal lipid per gram of body weight to about 10 μg of liposomal lipid per gram of body weight, the administered liposomes are predominantly taken up by parenchymal cells (at least 75%). These liposomes were shown by blood-clearance studies to have a half-life in the circulation of at least 8 hours (FIG. 1).

The study suggests that SUV meeting the requirements of having a half-life in the circulation of at least 8 hours and of being small enough to diffuse through the hepatic endothelial barrier and to enter hepatocytes via the endocytotic pathway can be used as an effective vehicle to target substances such as drugs to hepatocytes in vivo. The results also indicate that a blocking dose of about 7 μg liposomal lipid per g of body weight to about 10 μg liposomal lipid per g of weight is adequate to achieve such a targeting effect.

TABLE 1

CELLULAR DISTRIBUTION OF SM-CH SUV IN RAT LIVERS

| Lipid Dose (μg/g) | Percentage Distribution in: | | |
|---|---|---|---|
| | Hepatocytes | Kupffer Cells | Endothelial Cells |
| 0.003 ± 0.000 (n = 5) | 35.84% ± 15.54% | 41.17% ± 3.88% | 22.99% ± 16.89% |
| 0.342 ± 0.050 (n = 4) | 54.22% ± 12.16% | 42.44% ± 10.46% | 3.34% ± 2.98% |
| 1.576 ± 0.079 (n = 4) | 67.66% ± 16.48% | 25.89% ± 12.90% | 6.45% ± 4.99% |
| 6.788 ± 0.342 (n = 5) | 79.69% ± 10.21% | 17.05% ± 9.92% | 3.25% ± 4.83% |
| 7.605 ± 1.379 (n = 4) | 84.32% ± 10.28% | 14.20% ± 10.70% | 1.48% ± 1.87% |
| 97.500 ± 9.794 (n = 5) | 89.76% ± 5.60% | 8.43% ± 4.57% | 1.82% ± 1.59% |

The marker entrapped in SUV was $^{111}In^{3+}$-labeled inulin-DTPA. The standard deviation is listed immediately after the ± sign.

TABLE 2

CELLULAR DISTRIBUTION OF DSPC-CH SUV IN RAT LIVERS

| Lipid Dose (μg/g) | Percentage Distribution in: | | |
|---|---|---|---|
| | Hepatocytes | Kupffer Cells | Endothelial Cells |
| 0.003 ± 0.000 (n = 4) | 28.42% ± 5.05% | 65.73% ± 4.99% | 5.84% ± 4.32% |
| 0.159 ± 0.007 (n = 5) | 20.25% ± 18.35% | 65.78% ± 26.27% | 13.97% ± 12.33% |
| 1.908 ± 0.097 (n = 5) | 46.88% ± 23.07% | 30.22% ± 19.50% | 22.90% ± 20.45% |
| 9.944 ± 1.960 (n = 5) | 87.67% ± 11.46% | 10.59% ± 10.96% | 1.74% ± 0.97% |
| 104.260 ± 7.318 (n = 5) | 81.71% ± 6.83% | 10.59% ± 10.96% | 5.08% ± 3.05% |

The marker entrapped in SUV was $^{111}In^{3+}$-labeled inulin-DTPA. The standard deviation is listed immediately after the ± sign.

EXAMPLE 3

Effect of Simultaneous Administration of Large Multilamellar Liposomes on Distribution of Small Unilamellar Liposomes in Liver The procedure of Example 2 was followed, except that a varying dose of unlabeled large multilamellar liposomes (MLV) prepared from a 2:1 mixture of sphingomyelin and cholesterol was administered in addition to SUV prepared from the same lipid mixture. The SUV was administered at 0.150 μg lipid per gram of body weight. In this study, the liver cells of the animals receiving the liposomes were fractionated only into parenchymal and non-parenchymal cells; the non-parenchymal cells were not further fractionated into Kupffer cells and endothelial cells.

The results of the study are shown in Table 3. These results show that the administration of multilamellar large liposomes can selectively block the saturable pathway and result in a selective targeting of the unilamellar small liposomes to the hepatocytes, even at doses of the unilamellar liposomes well below the critical liposomal lipid dose.

TABLE 3

EFFECT OF DOSE OF SM-CH MLV ON CELLULAR DISTRIBUTION OF SM-CH SUV IN RAT LIVER

| MLV Dose (μg/g) | | Percentage Distribution in: | |
|---|---|---|---|
| | | Parenchymal Cells | Non-Parenchymal Cells |
| 0 | (n = 5) | 19.62% ± 5.45% | 80.38% ± 5.45% |
| 11.37 ± 0.38 | (n = 3) | 38.99% ± 1.75% | 61.01% ± 1.75% |
| 44.9 ± 1.69 | (n = 4) | 90.83% ± 5.56% | 9.17% ± 5.56% |
| 96.65 ± 10.83 | (n = 4) | 88.91% ± 6.82% | 11.09% ± 6.82% |

A varying dose of SM-CH MLV and a fixed dose of SUV (0.15 μg/g) were injected into rats via the tail vein. The cellular distribution of the SUV in the parenchymal and non-parenchymal cells was determined at 40 hours post-injection.

The method of selectively targeting substances to classes of cells in the liver achieves those goals that had been sought, and possesses a number of significant advantages over previous methods. It can selectively target the substance either to parenchymal cells or to non-parenchymal cells, as desired. It avoids conjugating galactose residues either to the substances themselves or to the liposomal carrier, eliminating the possibility of inactivation of the substance or undesirable allergic reactions. It does not require the administration of large quantities of excess lipid, and can be used with virtually any material to be targeted.

Although the present invention has been described in considerable detail with regard to certain preferred versions thereof, other versions are possible. Therefore, the spirit and scope of the appended claims should not be limited to the descriptions of the preferred versions contained herein.

What is claimed is:

1. A method for selectively targeting a substance to parenchymal cells of the liver of a mammalian body, comprising the steps of:
    (a) administering to the body a blocking agent for at least partially blocking uptake of liposomes by non-parenchymal cells of the liver; and
    (b) administering to the body the substance in carrier liposomes, the carrier liposomes being stable serum at 37° C., having a diameter of less than about 200 nm, and having a half-life in the circulation of the body of at least about 5 hours as measured at an injection dose of about 30–50 micrograms of lipid per gram of body weight, the substance being substantially taken up by the parenchymal cells.

2. The method of claim 1 wherein the step of administering the blocking agent comprises administration of an agent specifically inhibiting phagocytic activity.

3. The method of claim 1 wherein the blocking agent is non-carrier liposomes that do not carry the substrate, having a diameter greater than about 200 nm.

4. The method of claim 1 wherein the blocking agent is carbon particles.

5. The method of claim 1 wherein the blocking agent is heat-damaged or aged erythrocytes.

6. The method of claim 1 further comprising determining a critical liposomal lipid dose by measuring the distribution between parenchymal and non-parenchymal cells of the carrier liposomes as a function of the total quantity of lipid in the liposomes per unit of body weight; and
    wherein the step of administering the carrier liposomes comprises administering carrier liposomes having a total quantity of lipid per unit of body weight at least equal to the critical liposomal lipid dose.

7. The method of claim 1 wherein the carrier liposomes are unilamellar.

8. The method of claim 1 wherein the carrier liposomes are neutral.

9. The method of claim 1 wherein the carrier liposomes are selected from the group consisting of carrier liposomes composed of a mixture of sphingomyelin and cholesterol and carrier liposomes composed of a mixture of a phosphatidylcholine and cholesterol.

10. The method of claim 9 wherein the phosphatidylcholine is distearoylphosphatidylcholine.

11. The method of claim 1 wherein the substance is selected from the group consisting of polynucleotides, polypeptides, carbohydrates, and drugs.

12. The method of claim 11 wherein the substance is a drug.

13. The method of claim 12 wherein the drug is an antiviral agent.

14. The method of claim 6 wherein the critical liposomal lipid dose is between about 7 micrograms per gram of body weight and about 10 micrograms per gram of body weight.

15. A method for selectively targeting a substance to parenchymal cells of the liver of a human or animal body, comprising administering into the body the substance in carrier liposomes, the carrier liposomes being stable in serum at 37° C., having a diameter of less than about 200 nm, and having a half-life in the circulation of the body of at least about 5 hours as measured at an injection dose of about 30–50 micrograms per gram of body weight, the carrier liposomes being administered in a total quantity of lipid per unit of body weight at least equal to a critical liposomal lipid dose and less than about 15 micrograms of lipid per gram of body weight, the substance being taken up substantially by the parenchymal cells the critical liposomal lipid dose being determined by administering the substance in carrier liposomes at a range of injection doses and determining the mineral liposomal lipid dose at which the substance is taken up substantially the parenchymal liver cells.

16. The method of claim 15 wherein the carrier liposomes are unilamellar.

17. The method of claim 15 wherein the carrier liposomes are neutral.

18. The method of claim 15 wherein the carrier liposomes are selected from the group consisting of carrier liposomes composed of a mixture of sphingomyelin and cholesterol and carrier liposomes composed of a mixture of a phosphatidylcholine and cholesterol.

19. The method of claim 18 wherein the phosphatidylcholine is distearoylphosphatidylcholine.

20. The method of claim 15 wherein the substance is selected from the group consisting of polynucleotides, polypeptides, carbohydrates, and drugs.

21. The method of claim 13 wherein the critical liposomal lipid dose is between about 7 micrograms per gram of body weight and about 10 micrograms per gram of body weight.

22. A method for selectively targeting a substance to non-parenchymal cells of the liver of a mammalian body, comprising administering into the body the substance in carrier liposomes, the carrier liposomes being stable in serum at 37° C., having a diameter of less than about 200 nm, and having a half-life in the circulation of the body of at least about 5 hours as measured at an injection dose of about 30–50 micrograms of lipid per gram of body weight, the carrier liposomes having a total quantity of lipid per unit of body weight sufficiently lower than the critical liposomal lipid dose of the carrier liposomes that the substance is taken up predominantly by the non-parenchymal cells.

23. A method for selectively targeting a substance to the parenchymal cells of the liver of a mammalian body, comprising the steps of:
    (a) determining a critical liposomal lipid dose by measuring the distribution between parenchymal and non-parenchymal cells of carrier liposomes as a function of the total quantity of lipid in the liposomes per unit of body weight, the carrier liposomes being stable in serum at 37° C., having a diameter of less than about 200 nm and having a half-life in the circulation of the body of at least about 5 hours as measured at an injection dose of about 30–50 micrograms of lipid per gram of body weight, the liposomes being unilamellar and neutral and being composed of lipid mixtures selected from the group consisting of a mixture of sphingomyelin and cholesterol and a mixture of a phosphatidylcholine and cholesterol; and
(b) administering to the body the substance in the carrier liposomes in a total quantity of lipid per unit of body weight at least equal to the critical liposomal lipid dose, the substance being taken up predominantly by the parenchymal cells.

* * * * *